United States Patent
Spycher et al.

(10) Patent No.: US 10,709,493 B2
(45) Date of Patent: Jul. 14, 2020

(54) DISMANTLABLE MEDICAL INSTRUMENT

(71) Applicant: Karl Storz SE & Co. KG, Tuttlingen (DE)

(72) Inventors: Raphael Spycher, Eschenz (CH); Peter van Mil, Winterthur (CH)

(73) Assignee: Karl Storz SE & Co. KG, Tuttlingen (DE)

( * ) Notice: Subject to any disclaimer, the term of this patent is extended or adjusted under 35 U.S.C. 154(b) by 742 days.

(21) Appl. No.: 14/928,248

(22) Filed: Oct. 30, 2015

(65) Prior Publication Data
US 2016/0120586 A1 May 5, 2016

(30) Foreign Application Priority Data

Oct. 31, 2014 (DE) .................. 10 2014 115 873

(51) Int. Cl.
*A61M 1/00* (2006.01)
*A61B 90/00* (2016.01)
(Continued)

(52) U.S. Cl.
CPC .......... *A61B 18/1402* (2013.01); *A61B 17/32* (2013.01); *A61B 17/32002* (2013.01);
(Continued)

(58) Field of Classification Search
CPC ................ A61B 1/00105; A61B 3/185; A61B 5/150267; A61B 6/4411; A61B 8/4411;
(Continued)

(56) References Cited

U.S. PATENT DOCUMENTS 4,493,646 A * 1/1985 Lacour .................. A61C 1/18
433/133
5,088,984 A * 2/1992 Fields .................. A61M 39/14
604/167.02
(Continued)

FOREIGN PATENT DOCUMENTS

DE 624172 1/1936
DE 3227417 A1 2/1983
(Continued)

OTHER PUBLICATIONS

German Search Report Application No. 10 2014 115 873.3 Completed: Aug. 17, 2015; dated Aug. 21, 2015 2 pages.

*Primary Examiner* — Ronald Hupczey, Jr.
*Assistant Examiner* — Bradford C. Blaise
(74) *Attorney, Agent, or Firm* — Whitmyer IP Group LLC

(57) ABSTRACT

A dismantlable medical instrument including first, second and third components, a first bayonet connection for releasable mechanical connection of the third and second components, and a second bayonet connection for releasable mechanical connection of the third and first components. In a first predetermined position of the third component relative to the second component, the third component is not connected to the second component. In a second predetermined position of the third component relative to the second component, the third component is mechanically connected to the second component by the first bayonet connection, and the second and third components are not connected to the first component. In a third predetermined position of the third component relative to the second and first components, the third component is mechanically rigidly connected to the second component by the first bayonet connection and to the first component by the second bayonet connection.

19 Claims, 3 Drawing Sheets

(51) Int. Cl.
  *A61B 17/00* (2006.01)
  *A61B 18/14* (2006.01)
  *A61B 17/32* (2006.01)
  *A61B 18/00* (2006.01)

(52) U.S. Cl.
  CPC ............ *A61M 1/008* (2013.01); *A61B 90/08* (2016.02); *A61B 2017/0046* (2013.01); *A61B 2018/00053* (2013.01); *A61B 2018/0097* (2013.01); *A61B 2018/00172* (2013.01); *A61B 2018/00208* (2013.01); *A61B 2018/00577* (2013.01); *A61B 2018/1407* (2013.01); *A61B 2090/0813* (2016.02); *A61B 2217/005* (2013.01); *A61B 2217/007* (2013.01); *A61B 2218/001* (2013.01); *A61B 2218/002* (2013.01); *A61B 2218/007* (2013.01); *A61M 1/0086* (2014.02)

(58) Field of Classification Search
  CPC .... A61B 2560/0443; A61B 2017/0046; A61B 2018/00053; A61B 2018/00172; A61B 2018/00577; A61B 2018/0097; A61B 2217/005; A61B 2217/007; A61B 2218/001; A61B 2218/002; A61B 2218/007; A61B 90/08; A61B 2090/0813; A61M 1/0086
  See application file for complete search history.

(56) References Cited

U.S. PATENT DOCUMENTS

| | | | | |
|---|---|---|---|---|
| 5,407,293 | A * | 4/1995 | Crainich | A61B 17/29 |
| | | | | 403/322.1 |
| 6,126,359 | A * | 10/2000 | Dittrich | A61B 17/29 |
| | | | | 403/325 |
| 6,299,220 | B1 * | 10/2001 | Dittrich | A61B 1/00128 |
| | | | | 285/317 |
| 6,494,892 | B1 * | 12/2002 | Ireland | A61F 9/00763 |
| | | | | 604/22 |
| 7,561,352 | B2 * | 7/2009 | Dahmen | G02B 7/023 |
| | | | | 359/435 |
| 7,871,218 | B2 * | 1/2011 | Frey | G02B 23/2476 |
| | | | | 403/109.8 |
| 7,926,856 | B2 * | 4/2011 | Smutney | A61M 3/0279 |
| | | | | 285/330 |
| 8,490,250 | B2 * | 7/2013 | Lanz | B25G 1/04 |
| | | | | 16/427 |
| 2003/0201639 | A1 * | 10/2003 | Korkor | A61M 39/1011 |
| | | | | 285/81 |
| 2006/0271029 | A1 * | 11/2006 | Abboud | A61B 18/02 |
| | | | | 606/21 |
| 2012/0116433 | A1 * | 5/2012 | Houser | A61B 17/00234 |
| | | | | 606/169 |
| 2012/0277750 | A1 * | 11/2012 | Butsch | A61B 17/32002 |
| | | | | 606/84 |
| 2014/0142569 | A1 * | 5/2014 | Plascencia, Jr. | A61B 18/082 |
| | | | | 606/41 |

FOREIGN PATENT DOCUMENTS

| | | |
|---|---|---|
| DE | 102010050352 A1 | 5/2012 |
| EP | 1709932 A1 | 10/2006 |

* cited by examiner

DISMANTLABLE MEDICAL INSTRUMENT

FIELD OF THE INVENTION

The present invention relates to a dismantlable medical instrument, in particular to a dismantlable medical instrument with an integrated fluid channel through which, for example, ablated tissue can be sucked.

BACKGROUND OF THE INVENTION

Shavers and other medical instruments for mechanical and/or electrosurgical ablation of tissue often have an integrated fluid channel for irrigating the operating site or for suctioning the ablated tissue. A valve can be provided in order to control the flow of fluid and, therefore, the irrigating or suctioning effect. Particularly if ablated tissue is sucked through the fluid channel, the medical instrument, including the fluid channel, has to undergo thorough mechanical cleaning after each use. This applies in particular to a valve, with its relatively complex surface shapes, provided in the fluid channel.

SUMMARY OF THE INVENTION

An object of the present invention is to make available an improved dismantlable medical instrument which can be dismantled as much as possible, and in particular in a very simple way, in order to make a complete clean easier.

This object is achieved by the subject matter of the independent claim.

Developments are set forth in the dependent claims.

A dismantlable medical instrument comprises a first component, a second component, a third component, a first bayonet connection mechanism for releasable mechanical connection of the third component to the second component by a first bayonet connection, and a second bayonet connection mechanism for releasable mechanical connection of the third component to the first component by a second bayonet connection, wherein, in a first predetermined position of the third component relative to the second component, the third component is not connected to the second component, wherein, in a second predetermined position of the third component relative to the second component, the third component is mechanically connected to the second component by the first bayonet connection, and the second component and the third component are not connected to the first component, and wherein, in a third predetermined position of the third component relative to the second component and to the first component, the third component is mechanically rigidly connected to the second component by the first bayonet connection and to the first component by the second bayonet connection.

A dismantlable medical instrument comprises a first component, a second component, a third component, which is permanently connected mechanically to the second component in such a way that the third component is rotatable relative to the second component, and a bayonet connection mechanism for releasable mechanical connection of the third component to the first component by a bayonet connection, wherein, in a first predetermined position of the third component relative to the first component, the third component is not connected to the first component, and wherein, in a second predetermined position of the third component relative to the first component, the third component is mechanically rigidly connected to the first component by the bayonet connection.

The third component is in particular permanently connected mechanically to the second component in such a way that the third component is rotatable relative to the second component. The first component and the second component are in particular designed such that there is only one predetermined position, of the second component relative to the first component, in which the third component can reach the first predetermined position and the second predetermined position relative to the first component. In this case, the first predetermined position of the third component relative to the first component is also a first predetermined position of the third component relative to the second component, and the second predetermined position of the third component relative to the first component is also a second predetermined position of the third component relative to the second component. The bayonet connection and the bayonet connection mechanism of the last-mentioned dismantlable medical instrument correspond to the second bayonet connection or the second bayonet connection mechanism of the embodiments and variants set out below.

The dismantlable medical instrument is in particular a shaver or another medical instrument for ablating tissue by mechanical and/or electrosurgical means. The first component comprises in particular a handle for manually holding, guiding and moving the dismantlable medical instrument during its intended use in the context of a medical procedure. The medical instrument is provided and designed to be substantially dismantled after each use, wherein in particular the first component, the second component and the third component can be separated non-destructively from one another. In the dismantled state, the medical instrument can be substantially or completely cleaned. This is because surfaces that lie between the first component and the second component or between the second component and the third component or between the first component and the third component in the assembled configuration are exposed in the dismantled state. In particular, surfaces of fluid channels or other cavities of the medical instrument also lie exposed and are therefore accessible for direct manual or mechanical cleaning.

A bayonet connection or bayonet coupling is a form-fit and generally releasable mechanical connection between two components that is releasable non-destructively without use of tools. A bayonet connection is produced by the components first being brought together in a translational movement (generally a purely translational movement without any associated rotational movement) and then being rotated relative to each other. By means of a reverse movement, i.e. first rotation and then translation, the two components can be separated from each other again.

The first bayonet connection mechanism comprises in particular one or more catches, webs or grooves on one of the two components involved, these elements being designed, arranged and provided to engage behind catches or webs on the other component involved or to engage in grooves on the other component involved. In particular, one of the two components involved has radially inwardly protruding catches or webs which can engage behind corresponding, radially outwardly protruding catches or webs or can engage in one or more radially outwardly open grooves on the other component involved.

After the medical instrument has been cleaned, the first component, the second component and the third component can be assembled in the intended manner in order to provide the intended functionality of the medical instrument. This is described below for the medical instrument in which the second component and the third component are not connected permanently to each other but instead by a first bayonet connection. In the medical instrument in which the second component and the third component are permanently connected mechanically to each other, steps for producing the first bayonet connection between the second component and the third component are omitted.

To assemble the medical instrument, provision is made in particular that the third component is first of all attached in a first predetermined position to the second component. The first predetermined position comprises a first predetermined angular position or spatial orientation of the third component relative to the second component, where the third component is brought close to the second component by means of a first and in particular rectilinear translational movement (without any associated rotational movement) until the third component has reached the first predetermined position relative to the second component.

Proceeding from the first predetermined position, and by means of a first purely rotational movement about a predetermined axis of rotation, the third component can be brought to the second predetermined position relative to the second component. In the second predetermined position of the third component relative to the second component, the third component and the second component are mechanically connected to each other to the extent that they are no longer separable from each other in a purely translational movement. The axis of rotation of the first rotational movement is in particular parallel to the direction of the preceding purely translational movement. With the first translational movement and the subsequent first rotational movement, the first bayonet connection is produced between the third component and the second component.

When the third component is mechanically connected to the second component by the first bayonet connection, the second component and the third component can be brought together as a structural group toward the first component. This is done in particular in a second rectilinear translational movement in a direction parallel to the axis of rotation of the first bayonet connection. In this purely translational movement, the second component, relative to the first component, in particular already reaches its final predetermined position relative to the first component for the intended use of the medical instrument.

With a subsequent second rotational movement of the third component relative to the second component and to the first component, the second bayonet connection is produced between the third component and the first component. The rotation takes place in particular about the axis of rotation of the first bayonet connection. With this second rotational movement, the third component reaches the third predetermined position relative to the second component and to the first component, in which position it is mechanically connected to the second component by the first bayonet connection and to the first component by the second bayonet connection.

The design of the dismantlable medical instrument with three components, which are connectable to each other by two bayonet connections, can permit very substantial dismantling and therefore substantial exposure of inner surfaces of the medical instrument and, consequently, very simple and complete cleaning. The releasable mechanical connection of the components by bayonet connections can permit easy and quick dismantling and subsequent assembly of the medical instrument even by untrained personnel.

The first bayonet connection between the third component and the second component means that it is not necessary to simultaneously handle three components not connected to one another. Instead, a maximum of two components have to be handled and moved relative to each other at any one time, namely first of all the second component and the third component and, thereafter, the first component and the structural group composed of the second component and the third component.

As a result of the indirect mechanical connection between the first component and the second component via the third component, it is not necessary for the first component and the second component to be rotated relative to each other at any time. This creates additional degrees of freedom in terms of design. For example, the second component can engage in the first component in a way that does not permit a rotation of the second component relative to the first component, thereby preventing a direct bayonet connection between the first component and the second component.

In a dismantlable medical instrument as described here, the second component is arranged between the first component and the third component when the medical instrument is assembled in the intended manner ready for operation.

In other words, the third component is arranged in particular on a face of the second component partly directed away from the first component. With an arrangement of the second component between the first component and the third component or an arrangement of the third component on a face of the second component directed away from the first component, direct contact between the first component and the third component is not excluded, of the kind that actually takes place in the area of the second bayonet connection mechanism.

The arrangement of the second component between the first component and the third component in particular creates a form-fit definition of the location of the second component and can substantially or completely suppress a movement of the second component relative to the first component and to the third component.

A dismantlable medical instrument as described here moreover comprises in particular a detent mechanism for holding the third component at least either in the second predetermined position or in the third predetermined position relative to the second component.

The detent mechanism comprises in particular a recess or depression, and a protruding mechanism that is movable counter to the restoring force of an elastic mechanism toward the recess or depression. In particular, the recess or depression is arranged on the third component, and the elastic mechanism and the protruding mechanism are arranged on the second component. Alternatively, the recess or depression is arranged on the second component, and the elastic mechanism and the protruding mechanism are arranged on the third component. For example, the elastic mechanism comprises a helical spring in a bore, wherein the protruding mechanism comprises a ball which is prevented, by form-fit engagement, from completely exiting the bore and is pushed, by the spring, into a position in which the ball partially juts out of the bore.

The detent mechanism simplifies the assembling of the dismantlable medical instrument, in particular since it holds the third component with form-fit engagement both in the second predetermined position and also in the third predetermined position and prevents accidental release of the first bayonet connection or the second bayonet connection. Moreover, the detent mechanism creates tactile and/or audible feedback indicating that the second or third predetermined position is reached, which likewise simplifies assembly.

A dismantlable medical instrument as described here moreover comprises in particular a mechanism for suppressing a rotation of the second component relative to the first component when the third component is located in the third predetermined position.

In a dismantlable medical instrument as described here, the mechanism for suppressing a rotation comprises in particular a tubular stub on the second component and a corresponding opening on the first component or a tubular stub on the first component and a corresponding opening on the second component.

Alternatively, the mechanism for suppressing a rotation comprises, for example, a pin or a lug or another convex area provided on the second component and engaging in a corresponding opening on the first component, or a pin or a lug or another convex area provided on the first component and engaging in a corresponding opening on the second component.

A mechanism for suppressing a rotation of the second component relative to the first component can effect a predetermined orientation of the second component relative to the first component and prevent inadvertent release of the second bayonet connection between the third component and the first component. For example, a tubular stub and a corresponding opening can engage one in the other in a direction parallel to the axis of rotation of the bayonet connections, wherein the tubular stub and the opening are not rotationally symmetrical with respect to the axis of rotation. In particular, the tubular stub and the opening are spaced apart from the axis of rotation of the bayonet connections.

A tubular stub and a corresponding opening can in particular create a fluidic connection between the first component and the second component.

In a dismantlable medical instrument as described here, the first component and the second component each comprise one or more portions of a fluid channel for transporting a fluid, wherein the portions of the fluid channel are accessible for cleaning in the dismantled state of the medical instrument.

In particular, the first component and the second component each comprise parts of a fluid channel for transporting a fluid suctioned from an operating site, which fluid may, for example, contain ablated tissue.

In particular, the abovementioned tubular stub and the abovementioned opening, in which the tubular stub can engage, form parts of a fluid channel in the medical instrument.

In a dismantlable medical instrument as described here, the medical instrument is provided and designed in particular for ablation of tissue, and the fluid channel is provided and designed in particular to suction ablated tissue.

The dismantlable medical instrument is designed in particular as a shaver with a blade or a wire loop to which a high-frequency voltage can be applied in order to ablate tissue mechanically and/or electrosurgically. The blade or the wire loop can be rotatable by a motor that is provided in or on the medical device.

A dismantlable medical instrument as described here in particular further comprises a valve for partially or completely interrupting the fluid channel in the second component.

The valve can be provided and designed to switch on and off, modify, control or regulate the suction power or, in the case of a fluid channel that transports irrigation fluid, the irrigation power. As a result of the medical instrument being able to be dismantled, in particular as a result of the second component being separable from the first component, inner surfaces of the valve can be exposed and made accessible for mechanical cleaning.

In a dismantlable medical instrument as described here, the first component in particular has a protruding area, wherein the second component is substantially ring-like, and wherein the second component encloses the protruding area on the first component when the medical instrument is assembled in the intended manner ready for operation.

In a dismantlable medical instrument as described here, the third component is in particular substantially ring-like, wherein the third component encloses the protruding area on the first component when the medical instrument is assembled in the intended manner ready for operation.

A component is ring-like when, in the mathematical sense, it is contiguous several times (in particular twice) or has the topology of a circular ring. The component does not have to be in the shape of a circular ring or, for example, have the shape of a torus. A ring-like component, however, has an opening which passes right through the component and into which the protruding area on the first component can be inserted.

In a dismantlable medical instrument as described here, the second component and the third component, in their configuration when connected by the first bayonet connection, enclose in particular a substantially circular cylindrical interior.

The protruding area on the first component has in particular a shape corresponding to the interior enclosed by the second component and by the third component.

The axis of rotation of the bayonet connections and the directions of translation of the bayonet connections are in particular parallel to or identical to a longitudinal axis or an axis of symmetry of the protruding area on the first component.

In a dismantlable medical instrument as described here, particularly in the protruding area, a first portion of the fluid channel is arranged substantially parallel to the longitudinal axis of the protruding area, and a second portion of the fluid channel is arranged substantially perpendicularly with respect to the longitudinal axis of the protruding area, The protruding area on the first component thus contains an L-shaped or T-shaped part of the fluid channel.

A dismantlable medical instrument as described here moreover comprises in particular two seals which each annularly enclose the protruding area on the first component, wherein the second portion of the fluid channel ends in an opening between the seals.

The seals each enclosing the protruding area on the first component like a ring are, for example, O-rings located in corresponding ring-like, circular grooves that open outward and/or in the axial direction. The ring-like seals can be integrally bonded to the first component by vulcanization or in another way.

In a dismantlable medical instrument as described here, the second component is in particular designed to bear sealingly on both seals when the medical instrument is assembled in the intended manner ready for operation.

In a dismantlable medical instrument as described here, the second portion of the fluid channel has in particular an opening on each of two opposite sides of the protruding area on the first component.

The branches of the fluid channel that are formed by the two openings can be brought together again via an annular cavity between the first component and the second component and between the two seals. The two openings can greatly simplify cleaning of the fluid channel since, for example, a brush or a stream of cleaning fluid is guided transversely through the protruding area from one of the two openings to the other.

In a method for assembling a dismantlable medical instrument, a third component and a second component are connected to each other by a first bayonet connection, and then the third component is connected to a first component by a second bayonet connection.

The method can in particular be applied to or carried out in a dismantlable medical instrument as described here.

BRIEF DESCRIPTION OF THE DRAWINGS

Embodiments are explained in more detail below with reference to the attached figures, in which.

DETAILED DESCRIPTION OF THE INVENTION

Figure 1:
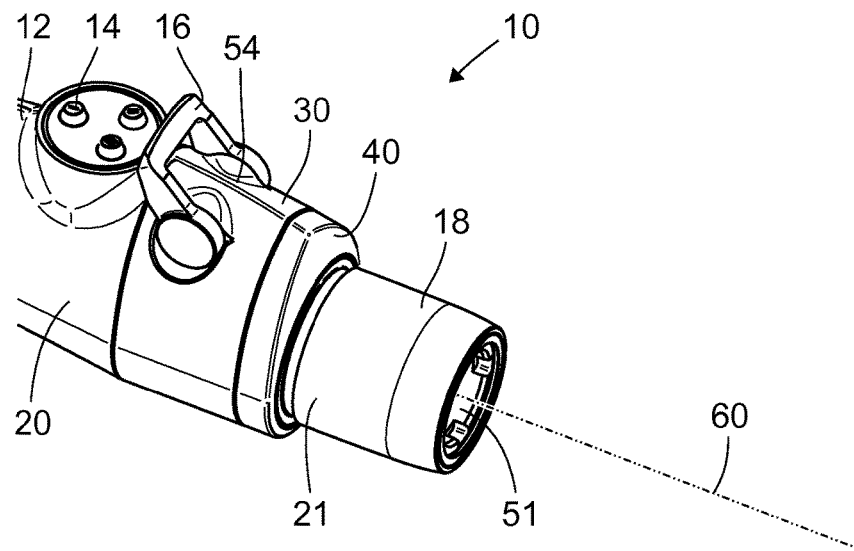
FIG. 1 shows a schematic axonometric view of a dismantlable medical instrument.

FIG. 1 shows a schematic axonometric view of a dismantlable medical instrument or of part of a dismantlable medical instrument 10 with a handle 12 in a proximal area of the dismantlable medical instrument 10. One or more keys, pushbuttons, switches or other operating elements 14 and a valve-actuating lever 16 are arranged near the handle 12. The dismantlable medical instrument 10 is in particular a shaver for mechanical and/or electrosurgical ablation of tissue. The operating elements 14 are provided, for example, for selecting an operating mode, for switching on and off a high voltage and/or a motor drive of an oscillating or rotating tool or for modifying the frequency, voltage or speed.

The illustrated part of the dismantlable medical instrument 10 comprises, at its distal end (to the right in FIG. 1), a substantially circular cylindrical coupling area for mechanical coupling to a tool or to a proximal end of a shank, of which the distal end has a tool or is connectable to a tool. In the coupling area 18, the dismantlable medical instrument 10 has a first portion 51 of a fluid channel for suctioning ablated tissue. The first portion 51 of the fluid channel extends in the axial direction of the substantially circular cylindrical coupling area 18. Only the inlet of the first, axial portion 51 of the fluid channel is discernible in FIG. 1.

The part of the dismantlable medical instrument 10 shown in FIG. 1 has three components 20, 30, 40. A protruding area 21, which comprises the coupling area 18, is provided on the first component 20. The second component 30 and the third component 40 are each ring-shaped and each enclose the protruding area 21.

The part of the medical instrument 10 shown in FIG. 1 can be dismantled into the components 20, 30, 40 non-destructively and without using tools and can be easily and quickly assembled from the components 20, 30, 40 without using tools. The assembling of the components 20, 30, 40 is described with reference to FIGS. 2 to 5.

Figure 2:
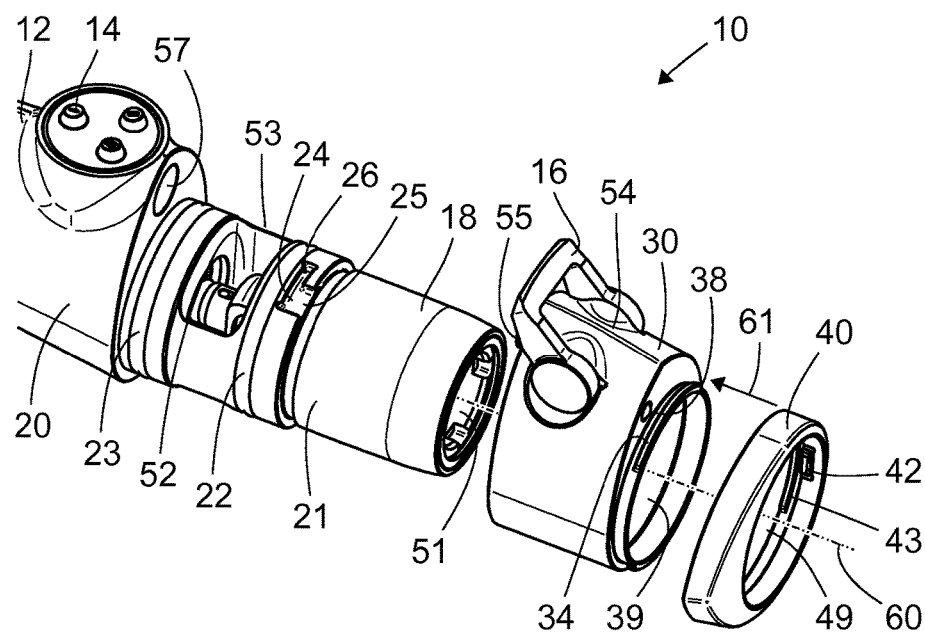
FIG. 2 shows a further schematic axonometric view of the dismantlable medical instrument from FIG. 1.

FIG. 2 shows a further schematic axonometric view of the components 20, 30, 40 of the dismantlable medical instrument 10 from FIG. 1. In FIG. 2, the components 20, 30, 40 are shown spaced apart from one another but in the relative orientation in which they can be assembled, as described with reference to FIGS. 4 to 7.

Setting aside features described below in particular, the protruding area 21 on the first component 20 has substantially the shape of a circular cylinder with an axis of symmetry 60. In the proximal direction from the coupling area 18, or between the handle 12 and the coupling area 18, the protruding area 21 on the first component 20 has two seals 22, 23, which each surround the protruding area 21 in a ring shape, particularly in a circular ring shape. The seals 22, 23 are, for example, O-rings in corresponding grooves which open out in the axial direction or, as in the example shown, in the radial direction. Alternatively, each of the two seals can be integrally bonded to the first component 20 by vulcanization.

Moreover, the protruding area 21 of the first component 20 has one or more L-shaped grooves 24, of which one is shown and visible in FIG. 2. The L-shaped groove 24 comprises an axial portion 25 parallel to the axis of symmetry 60 of the protruding area 21, and a portion 26 extending in the circumferential direction of the protruding area 21.

The second component 30 is substantially ring-shaped and encloses a substantially circular cylindrical interior 39, of which the cross section corresponds substantially to the cross section of the protruding area 21 on the first component 20. On its distal edge, the second component 30 has one or more webs 34 which are each arc-shaped and protrude radially outward, and of which one is shown and visible in FIG. 2. Moreover, the second component 30 has a detent mechanism 38 on its distal face directed toward the third component 40. The detent mechanism 38 comprises, for example, a ball in a bore, which ball is movable in the bore parallel to the axis of symmetry 60 but is prevented from completely exiting the bore by form-fit engagement and is pushed by a spring into a position in which the ball partially juts out of the bore.

The third component 40 comprises one or more webs 43 which are arc-shaped and protrude radially inward, and of which only one is shown and visible in FIG. 2. The arc-shaped webs 34 on the second component 30 and the arc-shaped webs 43 on the third component 40 are correspondingly designed and arranged such that the webs 34, 43 are able to engage one behind the other to produce a form-fit connection between the second component 30 and the third component 40. In particular, two webs are in each case arranged lying opposite each other both on the second component 30 and also on the third component 40 and extend in each case over slightly less than 90 degrees. The webs 34 on the second component 30 and the corresponding webs 43 on the third component 40 thus together form a first bayonet connection mechanism in order to produce a first bayonet connection between the second component 30 and the third component 40.

Moreover, one or more catches or lugs 42 which each protrude radially inward are arranged on the third component 40, of which only one is shown and visible in FIG. 2. In terms of their shape and their arrangement, the catches 42 on the third component 40 correspond to the L-shaped grooves 24 on the first component 20. By means of a translational movement and a subsequent rotational movement of the third component 40 relative to the first component 20, each catch 42 can be inserted initially through the axial portion 25 and then into the circumferentially extending portion 26 of the corresponding L-shaped groove 24. The grooves 24 on the first component 20 and the corresponding catches 42 on the third component 40 thus form a second bayonet connection mechanism for form-fit mechanical connection of the third component 40 to the first component 20 by a second bayonet connection.

As has already been mentioned, a first, axial portion 51 of a fluid channel is provided in the protruding area 21 on the first component 20 and extends, parallel or substantially parallel to the axis of symmetry 60 of the protruding area 21 on the first component 20, along the entire length or a great part of the length of the protruding area 21 on the first component 20. The first, axial portion 51 of the fluid channel has in particular a circular or substantially circular cross section.

A second, radial port on 52 of the fluid channel extends perpendicularly with respect to the axis of symmetry 60 of the protruding area 21 on the first component 20 from the first portion 51 as far as an opening 53 between the seals 22, 23 on the protruding area 21 on the first component 20. In the example shown, two second, radial portions 52 of the fluid channel are provided lying opposite each other and end in two mutually opposite openings 53 on the protruding area 21 of the first component 20. The two second, radial portions 52 of the fluid channel are formed in particular by a through-bore or a through-hole, which extends perpendicularly with respect to the axis of symmetry 60 of the protruding area 21 on the first component 20. Overall, the fluid channel 51, 52 inside the protruding area 21 on the first component 20 thus has a T-shaped configuration.

In the second component 30, a valve 54 is provided which can be opened and closed by pivoting the valve-actuating mechanism 16 about a pivot axis perpendicular to the axis of symmetry 60 of the protruding area 21 on the first component 20. Moreover, a tubular stub 55, which is almost completely concealed in FIG. 2, is provided on a face of the second component 30 directed toward the first component 20. The tubular stub 55 extends parallel or substantially parallel to the axis of symmetry 60 of the protruding area 21 on the first component 20. Arranged in the second component 30 is a substantially L-shaped portion of the fluid channel, which portion is not visible in FIG. 2, and in which the valve 54 and the tubular stub 55 lie.

An opening 57 corresponding to the tubular stub 55 on the second component 30 is provided on the first component 20, on an end face directed toward the second component 30. With the medical instrument 10 assembled in the intended manner ready for operation (cf. FIG. 1), the tubular stub 55 on the second component 30 engages in the opening 57 on the first component 20, and said L-shaped portion in the second component 30 connects the second, radial portion 52 of the fluid channel to the opening 57 in the first component 20. The assembled medical instrument 10 thus has a fluid channel whose constituent parts are the first, axial portion 51, the one or more second, radial portions 52, the valve 54, the tubular stub 55, and the opening 57 in the first component 20.

The fluid channel can be closed or interrupted and opened or freed by means of the valve 54 in the second component 30. If the opening 57 in the first component 20 is coupled to a suction pump or vacuum pump, for example, a suction action on the medical instrument 10 can be switched on and off by means of the valve-actuating lever 16 and the valve 54. Optionally, the valve 54 can be designed such that the suction action is adjustable steplessly or in steps. If the opening 57 in the first component 20 is coupled via a feed pump to a reservoir containing irrigation fluid, a flow of irrigation fluid in the dismantlable medical instrument 10 can be switched on and off, and optionally adjusted steplessly or in steps, by means of the valve-actuating lever 16 and the valve 54.

Figure 3:
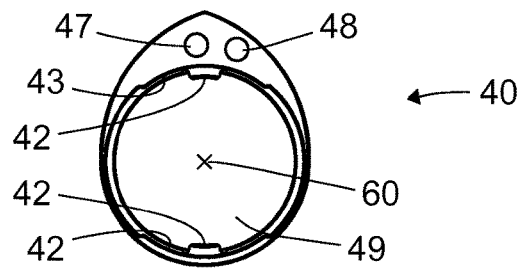
FIG. 3 shows a schematic view of a third component of the dismantlable medical instrument from FIGS. 1 and 2.

FIG. 3 shows a schematic view of the third component 40 of the medical instrument 10 described with reference to FIGS. 1 and 2. The end face of the third component 40 directed toward the second component 30 is visible in FIG. 3.

The ring-like or substantially ring-shaped third component 40 encloses a substantially circular or circular cylindrical interior 49, of which the cross section corresponds substantially to the cross section of the protruding area 21 on the first component 20. Two catches 42 on 40 jut into the interior 40. Two arc-shaped and inwardly protruding webs 43 lie opposite each other and in each case occupy an angle of almost 90 degrees and are separated by two gaps, which each extend over slightly more than 90 degrees. A first recess 47 and a second recess 48 are provided in the end face which is shown in FIG. 3 and which is directed toward the second component 30 (cf. FIG. 2), said recesses corresponding, in terms of their shape and their arrangement, to the detent mechanism 38 on the second component 30 (cf. FIG. 2).

Figure 4:
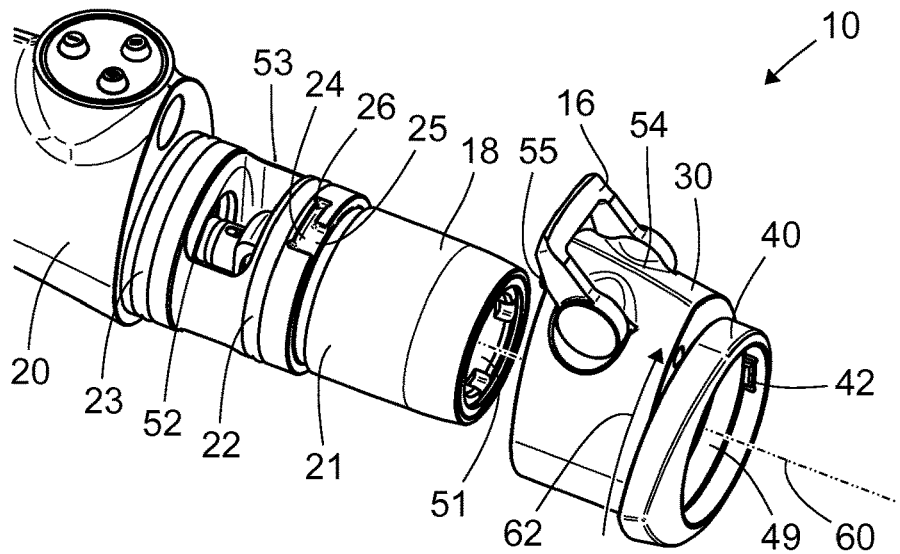
FIG. 4 shows a further schematic axonometric view of the dismantlable medical instrument from FIGS. 1 to 3.

FIG. 4 shows a further schematic axonometric view of the components 20, 30, 40 from FIGS. 1 to 3. The nature of the view corresponds to that of FIGS. 1 and 2.

The configuration shown in FIG. 4 differs from that shown in FIG. 2 in that the third component 40 is brought into a first predetermined position relative to the second component 30 by a first purely translational movement parallel to the axis of symmetry 60 relative to the second component 30. The first translational movement is indicated in FIG. 2 by an arrow 61.

In the first predetermined position of the third component 40 relative to the second component 30 as shown in FIG. 4, the second component 30 and the third component 40 are not yet mechanically connected to each other with form-fit engagement and instead can be separated again from each other by a purely translational movement.

Proceeding from the first predetermined position of the third component 40 relative to the second component 30 as shown in FIG. 4, the third component 40 can be brought to a second predetermined position (shown in FIG. 5) relative to the second component 30 by means of a first rotational movement, indicated by an arrow 62, about the axis of symmetry 60.

Figure 5:
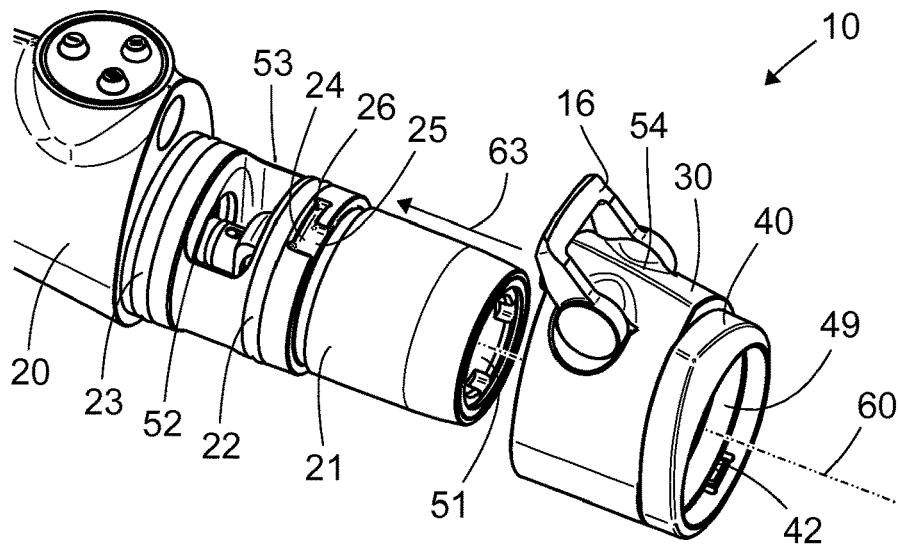
FIG. 5 shows a further schematic axonometric view of the dismantlable medical instrument from FIGS. 1 to 4.

FIG. 5 shows a further schematic axonometric view of the dismantlable medical instrument 10 from FIGS. 1 to 4. The nature of the view corresponds to that of FIGS. 1, 2 and 4.

The aforementioned second predetermined position of the third component 40 relative to the second component 30 is shown in FIG. 5. In this second predetermined position, the radially inwardly protruding webs 43 on the third component 40 partially engage behind the radially outwardly protruding webs 34 on the second component 30 (cf. FIGS. 2 and 3). In this way, a form-fit mechanical connection, specifically a first bayonet connection, is produced between the second component 30 and the third component 40 and cannot be separated again by a purely translational relative movement. The second component 30 and the third component 40 thus form a structural group.

In the second predetermined position of the third component 40 relative to the second component 30 as shown in FIG. 5, the detent mechanism 38 on the second component 30 (cf. FIGS. 2 and 4) engages in the first recess 47 on the third component 40 (cf. FIG. 3). In this way, the third component 40 is held elastically with form-fit engagement in the second predetermined position relative to the second component 30.

Figure 6:
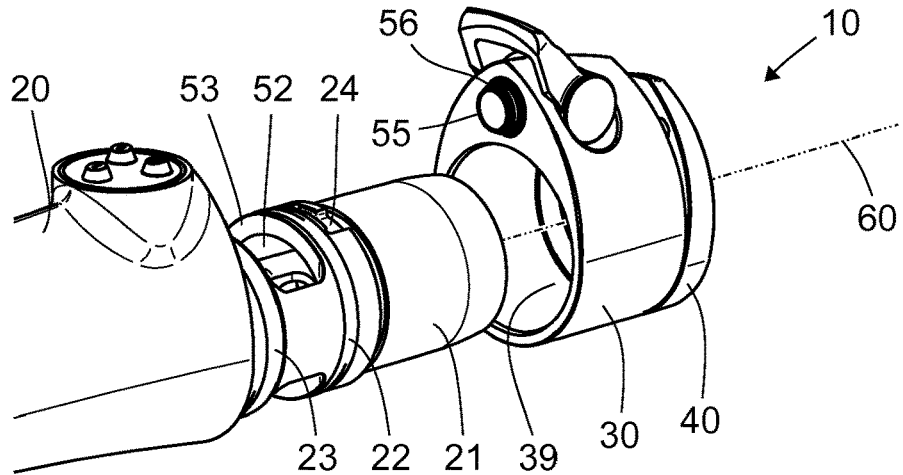
FIG. 6 shows a further schematic axonometric view of the dismantlable medical instrument from FIGS. 1 to 5.

FIG. 6 shows a further schematic axonometric view of the first component 20 and of the structural group formed by the second component 30 and the third component 40, from a somewhat different perspective and viewing direction.

The tubular stub 55 on the end face of the second component 30 directed toward the first component 20 is visible in FIG. 6. A seal 56, made of an elastomer or of another elastic material, is provided on the outer circumference of the tubular stub 55 and is integrally bonded to the second component 30, for example by vulcanization. The seal 56 here forms almost the entire outer surface of the tubular stub 55 or at least a part thereof.

The entire outer surface of the tubular stub 55, or the part of the outer surface of the tubular stub 55 formed by the seal 56, is cone-shaped, for example, or has the shape of a cutout of a jacket surface of a circular cone. Alternatively, the outer contour of the cross section of the seal 56 or of the entire tubular stub can have steps, for example, or a stair formation. In this case, with the medical instrument 10 assembled in the intended manner ready for operation (cf. FIG. 1), the seal 56 can bear in a plurality of narrow annular areas at the edge of the opening 57 (cf. FIGS. 2, 4 and 5). In this way, the sealing action of the seal 56 can be improved.

In addition to its sealing action, the seal 56 can optionally provide tolerance compensation between the first component 20 and the second component 30. The first component 20 and the second component 30 are in particular designed such that they have a predetermined play, so as to be able to be assembled with minimal friction. This play can be partially or completely canceled by the elasticity of the seal 56.

Proceeding from the configuration shown in FIGS. 5 and 6, the structural group composed of the second component 30 and of the third component 40 can be attached to the first component 20 by a second purely translational movement, which is indicated by an arrow 63 in FIG. 5.

Figure 7:
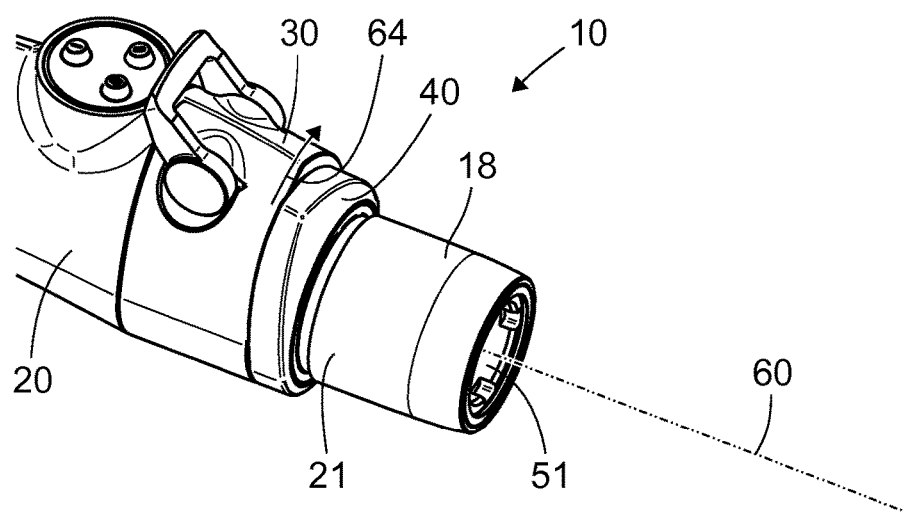
FIG. 7 shows a further schematic axonometric view of the dismantlable medical instrument from FIGS. 1 to 6.

FIG. 7 shows a further schematic axonometric view of the components 20, 30, 40 from FIGS. 1 to 6. The nature of the view corresponds to that of FIGS. 1, 2, 4 and 5.

FIG. 7 shows the configuration which, proceeding from the configuration shown in FIGS. 5 and 6, is reached when the structural group composed of the second component 30 and of the third component 40 is moved in the second translational movement, indicated by the arrow 63 in FIG. 5, relative to the first component 20. In this second translational movement, the catches 42 on the third component 40 (cf. FIGS. 2 to 5) are moved in the axial portions 25 of the L-shaped grooves 24.

In the configuration shown in FIG. 7, the tubular stub 55 on the second component 30 (cf. FIG. 6) engages in the opening 57 on the first component 20 (cf. FIGS. 2, 4 and 5), and the seal 56 on the second component 30 bears sealingly in one or more annular areas at the edge of the opening 57 on the first component 20. Moreover, in the configuration shown in FIG. 7, the wall face of the substantially circular cylindrical interior 39 of the second component 30 (cf. FIGS. 2 and 6 in particular) bears sealingly on the seals 22, 23 on the protruding area 21 on the first component 20 (cf. FIGS. 2, 4, 5 and 6). In this way, the aforementioned fluid channel in the interior of the medical instrument 10 is produced in its entirety and is sealed off from the outside.

In the configuration shown in FIG. 7, however, the structural group composed of the second component 30 and of the third component 40 can be separated from the first component 20 by means of a simple translational movement parallel to the axis of symmetry 60 of the protruding area 21 on the first component 20. In this process, the catches 42 on the third component 40 (cf. FIGS. 2 to 5) would be moved only in the axial portions 25 of the L-shaped grooves 24.

Proceeding from the configuration shown in FIG. 7, the third component 40 can be connected to the first component 20 by means of a second rotational movement 64 (indicated by an arrow 64) relative to the first component 20 and to the second component 30. In this process, the catches 42 on the third component 40 (cf. FIGS. 2 to 5) are moved into those portions 26 of the L-shaped grooves 24 that extend in the circumferential direction of the protruding area 21 of the first component 20, and the third component 40 reaches the third predetermined position relative to the first component 20 and to the second component 30 as shown in FIG. 1.

In the third predetermined position of the third component 40 relative to the second component 30 as shown in FIG. 1, the detent mechanism 38 on the second component 30 (cf. FIGS. 2 and 4) engages in the second recess 48 on the third component 40 (cf. FIG. 3). In this way, the third component 40 is held with a latching action, or with an elastic form-fit engagement, in the third predetermined position relative to the second component 30 as shown in FIG. 1 (and indirectly also relative to the first component 20).

In this third predetermined position, a form-fit connection between the third component 40 and the first component 20 is created by the catches 42 on the third component 40 (cf. FIGS. 2 to 5) engaging in those portions 26 of the L-shaped grooves 24 that extend in the circumferential direction of the protruding area 21 of the first component 20. This form-fit connection cannot be separated by a simple translational movement. The L-shaped grooves 24 on the protruding area 21 on the first component 20 and the corresponding catches 42 on the third component 40 form a second bayonet connection mechanism for the form-fit engagement and non-destructive releasable mechanical connection of the first component 20 to the third component 40 by a second bayonet connection.

By means of the first bayonet connection between the second component 30 and the third component 40 and the second bayonet connection between the third component 40 and the first component 20, the first component 20 and the third component 40 are also indirectly connected mechanically rigidly to each other. In addition, the arrangement of the second component 30 between the first component 20 and the third component 40 suppresses a translational movement, and the form-fit engagement between the tubular stub 55 on the second component 30 and the opening 57 in the first component 20 suppresses a rotational movement of the second component 30 relative to the first component 20.

What is claimed is:

1. A dismantlable medical instrument comprising:
a first component, a second component, a third component, a first bayonet connection mechanism for releasable mechanical connection of the third component to the second component by a first bayonet connection,
the first component having a protrusion, the protrusion being disposed within an opening in the second component and within an opening in the third component when the first, second and third components are connected,
a second bayonet connection mechanism for releasable mechanical connection of the third component to the first component by a second bayonet connection, wherein a portion of the second bayonet connection is comprised of a portion of the protrusion, a rotational axis about which the first and second bayonet connections rotate to engage the third component to the second component and the third component to the first component, wherein, in a first predetermined position of the third component relative to the second component, the third component is not connected to the second component, wherein, in a second predetermined position of the third component relative to the second component, the third component is in a first rotational position about the rotational axis, in relation to the second component, the third component is mechanically connected to the second component by the first bayonet connection, and the second component and the third component are not connected to the first component, wherein, in a third predetermined position of the third component relative to the second component and to the first component, the third component is in a second rotational position about the rotational axis, in relation to the second component, the third component is mechanically rigidly connected to the second component by the first bayonet connection and to the first component by the second bayonet connection, wherein the second rotational position is different from the first rotational position.

2. The dismantlable medical instrument according to claim 1, wherein the second component is arranged between the first component and the third component when the medical instrument is assembled for operation.

3. The dismantlable medical instrument according to claim 1, further comprising:
a detent mechanism for holding the third component at least either in the second predetermined position or in the third predetermined position relative to the second component.

4. The dismantlable medical instrument according to claim 3, wherein the detent mechanism is on an axial wall of the third component.

5. The dismantlable medical instrument according to claim 1, further comprising:
a mechanism for suppressing a rotation of the second component relative to the first component when the third component is located in the third predetermined position.

6. The dismantlable medical instrument according to claim 5, wherein the mechanism for suppressing a rotation comprises a tubular stub on the second component and a corresponding opening on the first component, or a tubular stub on the first component and a corresponding opening on the second component.

7. The dismantlable medical instrument according to claim 6, wherein the tubular stub and the corresponding opening on the first component engage one another to provide a fluid connection.

8. The dismantlable medical instrument according to claim 1, wherein the first component and the second component each comprise one or more portions of a fluid channel for transporting a fluid, wherein the one or more portions of the fluid channel are accessible for cleaning in a dismantled state of the medical instrument.

9. The dismantlable medical instrument according to claim 8, further comprising:
a valve for partially or completely interrupting the fluid channel in the second component.

10. The dismantlable medical instrument according to claim 9, wherein the valve is actuated by a lever on an outer surface of the second component.

11. The dismantlable medical instrument according to claim 8, wherein the one or more portions of the fluid channel of the first component include a radial port.

12. The dismantlable medical instrument according to claim 1, wherein
the second component is substantially ring-like,
the second component encloses the protrusion on the first component when the medical instrument is assembled for operation.

13. The dismantlable medical instrument according to claim 12, wherein
the third component is substantially ring-like,
the third component encloses the protrusion on the first component when the medical instrument is assembled for operation.

14. The dismantlable medical instrument according to claim 13, wherein,
the first component and the second component each comprise one or more portions of a fluid channel for transporting a fluid, wherein the portions of the fluid channel are accessible for cleaning in the dismantled state of the medical instrument;
in the protrusion on the first component, a first portion of the fluid channel is arranged substantially parallel to the longitudinal axis of the protrusion, and a second portion of the fluid channel is arranged substantially perpendicular to the longitudinal axis.

15. The dismantlable medical instrument according to claim 14, further comprising:
two seals which each annularly enclose the protrusion on the first component, wherein the second portion of the fluid channel ends in an opening between the seals.

16. The dismantlable medical instrument according to claim 14, wherein the second portion of the fluid channel has an opening on each of two opposite sides of the protrusion on the first component.

17. A dismantlable medical instrument comprising:
a first component, a second component, a third component, a first bayonet connection mechanism for releasable connection of the third component to the second component by a first bayonet connection;
the first component having a protrusion, the protrusion being disposed within an opening in the second component and within an opening in the third component when the first, second, and third components are connected,
a second bayonet connection mechanism for releasable mechanical connection of the third component to the first component by a second bayonet connection, wherein a portion of the second bayonet connection is comprised of a portion of the first protrusion;
a rotational axis about which the first and second bayonet connections rotate to engage the third component to the second component and the third component to the first component;
wherein, in a first position, the third component and the second component are in contact with the first component, the first and second bayonet connections are disengaged;
wherein, in a second position, the second component and the third component are in contact with the first component, the third component is rotated less than 360 degrees in a first rotational direction relative to the first position, the first bayonet connection is engaged, the third component is rigidly connected with the second component, the second bayonet connection is disengaged, and the third component is in a first rotational position about the rotational axis, in relation to the second component; and wherein, in a third position, the second component is rigidly connected to the third component, the third component is rigidly connected to the first component and the third component is rotated less than 360 degrees in the first rotational direction relative to the second position to engage the second bayonet connection, and the third component is in a second rotational position about the rotational axis, in relation to the second component;

wherein the second rotational position is different from the first rotational position.

18. A dismantlable medical instrument comprising:

a first component, a second component, a third component, the first component having a protrusion being disposed within an opening in the second component and within an opening in the third component when the first, second, and third components are connected, a detent mechanism for releasable connection of the third component to the second component, a bayonet connection for releasable mechanical connection of the third component to the first component, wherein a portion of the bayonet connection is comprised of a portion of the protrusion, a rotational axis about which the bayonet connection rotates to engage the third component to the first component, wherein in a first predetermined position of the third component relative to the second component and to the first component, the third component is mechanically connected to the second component by the detent mechanism, and to the first component by the bayonet connection, the third component is in a first rotational position about the rotational axis, in relation to the second component, wherein, in a second predetermined position of the third component relative to the second component, the third component is mechanically connected to the second component by the detent mechanism, the second component and the third component are not connected to the first component, and the third component is rotated about the rotational axis by less than 360 degrees relative to the first predetermined position, and the third component is in a second rotational position about the rotational axis, in relation to the second component, wherein, in a third predetermined position of the third component relative to the second component, the third component is not connected to the second component, and wherein the second rotational position is different from the first rotational position.

19. The dismantlable medical instrument according to claim 18, wherein in the third predetermined position, axial surfaces and inner surfaces of the second component, and axial surfaces and inner surfaces of the third component are exposed.

* * * * *